(12) United States Patent
Yeh (10) Patent No.: US 10,149,944 B2
(45) Date of Patent: Dec. 11, 2018

(54) SYRINGE

(71) Applicant: CC Biotechnology Corporation, Tainan (TW)

(72) Inventor: Chin-Min Yeh, Tainan (TW)

(73) Assignee: CC Biotechnology Corporation, Tainan (TW)

( * ) Notice: Subject to any disclaimer, the term of this patent is extended or adjusted under 35 U.S.C. 154(b) by 293 days.

(21) Appl. No.: 15/274,814

(22) Filed: Sep. 23, 2016

(65) Prior Publication Data

US 2017/0007773 A1    Jan. 12, 2017

(51) Int. Cl.
*A61M 5/315*    (2006.01)
*A61M 5/32*    (2006.01)
*A61M 5/24*    (2006.01)
*A61M 5/31*    (2006.01)

(52) U.S. Cl.
CPC .... *A61M 5/31528* (2013.01); *A61M 5/31555* (2013.01); *A61M 5/31575* (2013.01); *A61M 5/31585* (2013.01); *A61M 5/3202* (2013.01); *A61M 5/24* (2013.01); *A61M 5/3129* (2013.01)

(58) Field of Classification Search
CPC .......... A61M 5/31555; A61M 5/31575; A61M 5/31585; A61M 5/31528; A61M 5/24; A61M 5/2422; A61M 5/315; A61M 5/31501; A61M 5/31511; A61M 2005/2407; A61M 2005/2403; A61M 2005/2485; A61M 2005/2488; A61M 2005/2492; A61M 2005/31508; A61M 2005/3152; A61M 5/31525; A61M 5/31526; A61M 5/3153; A61M 5/31533; A61M 5/31566; A61M 5/31576; A61M 5/31578; A61M 5/3158; A61M 5/31583; A61M 5/178
See application file for complete search history.

(56) References Cited

U.S. PATENT DOCUMENTS

| 2,660,168 A | 11/1953 | Pontius |
| 3,136,313 A | 6/1964 | Enstrom et al. |
| 2006/0184117 A1 | 8/2006 | Knight et al. |

(Continued)

FOREIGN PATENT DOCUMENTS

| CN | 102083489 A | 6/2011 |
| CN | 102497900 A | 6/2012 |

(Continued)

*Primary Examiner* — Kevin C Sirmons
*Assistant Examiner* — Leah Swanson
(74) *Attorney, Agent, or Firm* — C. G. Mersereau; Nikolai & Mersereau, P.A.

(57) ABSTRACT

A syringe is applied to connect with a vial and a needle, and the syringe includes an outer protecting housing, a connecting ring, a vial housing, an inner tube, a bidirectional guiding tube device, a screwing sleeve, a ratchet, a spiral rotating rod and an injection rod unit. The connecting ring is mounted on a front end of the outer protecting housing, and the vial housing is connected with the connecting ring for assembling a vial. The inner tube, the bidirectional guiding tube device, the screwing sleeve, the ratchet, the spiral rotating rod and the injection rod unit are mounted in the outer protecting housing. The injection rod unit is rapidly pulled backward and then is pressed to move forward for injecting.

10 Claims, 8 Drawing Sheets

(56) References Cited

U.S. PATENT DOCUMENTS

2010/0268171 A1* 10/2010 Moller .............. A61M 5/31551
  604/246
2014/0249482 A1* 9/2014 Wieselblad ....... A61M 5/31551
  604/211
2016/0129196 A1* 5/2016 Hirschel ........... A61M 5/31541
  604/211

FOREIGN PATENT DOCUMENTS

| CN | 102648013 A | 8/2012 |
| CN | 203090111 U | 7/2013 |
| TW | M447779 U | 3/2013 |
| TW | M461437 U | 9/2013 |
| TW | M466672 U | 12/2013 |
| TW | M483803 U | 8/2014 |
| WO | 2013058698 A1 | 4/2013 |

* cited by examiner

SYRINGE

BACKGROUND OF THE INVENTION

1. Field of the Invention

The present invention relates to a medical apparatus, especially to a syringe having a function that safely controls the injection dose and a function that is laborsaving in operation.

2. Description of Related Art

In order to achieve multiple purposes such as dose metering, injection time counting, and repeatable using, the conventional syringes include two kinds: a dose metering syringe and a frequency measuring syringe. The structure of the conventional dose metering syringe mainly includes a driving device assembled by multiple driving components mounted in a barrel and connected with a piston rod. A vial is assembled in the barrel. A needle is mounted on a front end of the barrel and is connected with the vial for injecting. When the syringe is in an injecting process, the needle is pierced into the skin or the veins of a human body, the driving device is driven by pushing the piston rod to inject the medication. The dose of the injection can be controlled by the driving device and the movement of the piston rod to achieve the purpose of dose-metering.

Although the dose metering syringe already achieves the purpose of dose-metering, the dose metering syringe still has a laborious issue because the components of the driving device restrict the movement of each other and the driving device requires a lot of effort to use.

To overcome the shortcomings of the conventional dose metering syringe, the present invention provides a syringe to mitigate or obviate the aforementioned problems.

SUMMARY OF THE INVENTION

The main objective of the present invention is to provide a syringe used for connecting with a vial and a needle, comprising:

an outer protecting housing being tubular and having two openings respectively in a front end and a rear end of the outer protecting housing;

a connecting ring mounted on the front end of the outer protecting housing and having an inner ring portion, a ratchet portion formed around in the inner ring portion and having multiple inclined teeth;

a vial housing mounted on a front end of the connecting ring for fixing the vial inside, the needle detachably mounted on a front end of the vial housing;

an inner tube mounted in the outer protecting housing, a front end of the inner tube fixed in the connecting ring;

a bidirectional guiding tube device including an outer guiding tube having a mounting tube and an end tube formed in a front end of the mounting tube; a spiral recess formed in an inner surface of the mounting tube; multiple ratchet pawls mounted around an outer surface of the end tube and engaged with the ratchet portion of the connecting ring to limit the outer guiding tube to rotate toward one single direction; and an inner guiding tube mounted between the outer guiding tube and the inner tube and having multiple spiral protrusions formed on an outer surface of a front segment of the inner guiding tube and mounted in the spiral recess to make the inner guiding tube rotate in the outer guiding tube for a predetermined movement distance; and a ratchet recess formed in a rear segment of the inner guiding tube and having multiple teeth;

a screwing sleeve mounted in the end tube of the outer guiding tube and having a screw hole formed in the screwing sleeve;

a ratchet mounted in the ratchet recess of the inner guiding tube and including a gear body and multiple ratchet pawls formed around an outer surface of the gear body, a central hole formed in the gear body, the ratchet pawls of the ratchet engaged with the teeth of the ratchet recess of the inner guiding tube;

a spiral rotating rod having a dose metering section having screw threads formed around the dose metering section, an axial hole formed in the spiral rotating rod, the spiral rotating rod mounted in the bidirectional guiding tube device, the dose metering section connected inside the screwing sleeve and extending into the vial to generate a push force; and an injection rod unit including an injecting rod including a rod body and a pushing end formed at a rear end of the rod body, the rod body axially movably mounted through the axial hole of the spiral rotating rod and fixed in the central hole of the ratchet, the rear end of the rod body that has the pushing end extending out of the inner guiding tube; and a cover mounted around the pushing end of the injecting rod, a rear end of the inner guiding tube pivotally mounted in the cover to combine the ratchet, the bidirectional guiding tube, the screwing sleeve and the spiral rotating rod for opening and closing repeatedly.

As in the afored-mentioned syringe, the inner tube has a restricting protrusion and a blocking pin formed in a rear end of the inner tube, the inner guiding tube has multiple restricting threaded grooves formed in an outer surface at spaced intervals, and has a guiding recess of a predetermined length; the restricting protrusion abuts the restricting threaded grooves of the inner guiding tube to block the inner guiding tube from moving forward; the restricting protrusion changes positions to abut the guiding recess, and the inner guiding tube can be driven to move forward; and the restricting protrusion limits the position of backward moving of the inner guiding tube.

As in the above-mentioned syringe, the shape of the axial hole of the spiral rotating rod corresponds to the shape of the rod body of the injecting rod, and both of the shapes are non-circular.

As in the above-mentioned syringe, the screwing sleeve has a positioning protrusion axially formed on an outer surface of the screwing sleeve; the outer guiding tube has a positioning channel axially formed in an inner surface of the end tube; the screwing sleeve is engaged with the outer guiding tube by the positioning protrusion corresponding to mount in the positioning channel.

As in the above-mentioned syringe, an assembling ring portion and a connecting ring portion are respectively formed in a front end and a rear end of the connecting ring; the connecting ring portion is inserted into the outer protecting housing; multiple hooks are formed between the inner ring portion and the connecting ring portion; the inner tube has multiple engaging recesses for the hooks to engage; an inner ring is mounted between the hooks and the inner ring portion to connect the inner tube and the connecting ring.

As in the above-mentioned syringe, a piston pushing block is mounted in a front end of the dose metering section of the spiral rotating rod.

The syringe of the present invention with the overall structure achieves some benefits. The vial and the needle are mounted in the syringe; the injection rod unit is rapidly pulled backward and then is pressed to move forward for injecting. A large pitch stroke of the bidirectional guiding tube device cooperates with a small pitch stroke of the screwing sleeve with the spiral rotating rod to transform a pressing force into a rotating force. The rotating force of a large stroke is transformed into an injecting force of a small stroke, to achieve not only the purpose of controlling medicine dosage but also increasing safety. When the syringe is in use, the injection rod unit is combined with the ratchet, the bidirectional guiding tube device, the screwing sleeve, and the spiral rotating rod to get benefits of labor-saving that the syringe repeats opening and closing in a dose metering injecting process.

The injection rod unit of the syringe must be pulled to a predetermined position by the combination structure of the restricting protrusion of the inner tube and the restricting threaded grooves of the inner guiding tube, and the injection rod unit can be pushed for injection. The inner guiding tube is restricted by the restricting threaded grooves engaged with the restricting protrusion of the inner tube to generate a blocking function, such that the injection rod unit and the inner guiding tube will not be retracted accidentally when the injection rod unit is pulled out. The injecting dose of the syringe is ensured to reach the predetermined injecting dose.

In addition, the syringe further includes a cap. The cap can be mounted on the syringe only when the needle is removed from the syringe, so as to ensure the needle is renewed for every use of the syringe.

DETAILED DESCRIPTION OF PREFERRED EMBODIMENT

Figure 1:
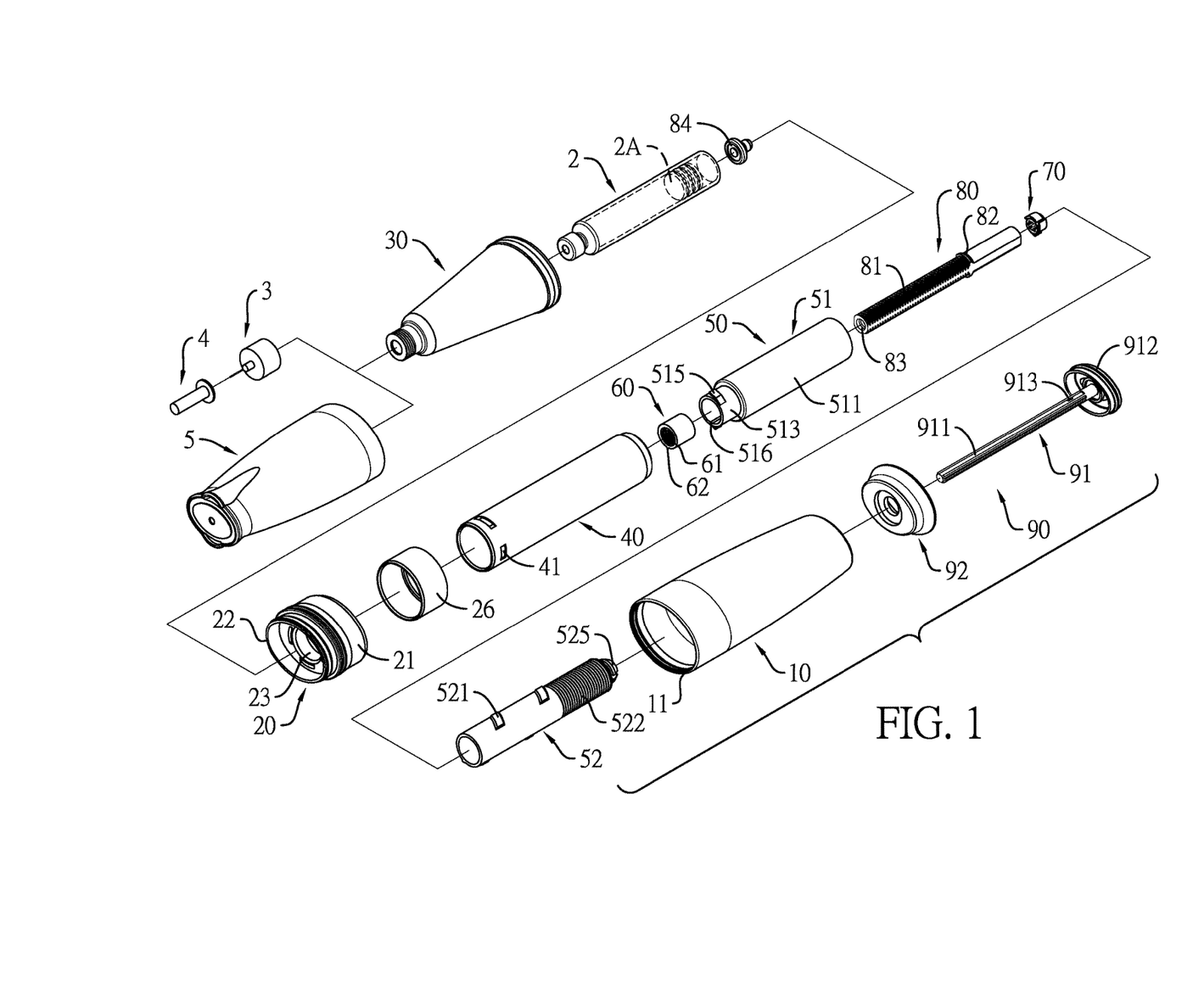
FIG. 1 is an exploded perspective view of a syringe with a needle and a needle cap in accordance with the present invention.
Figure 2:
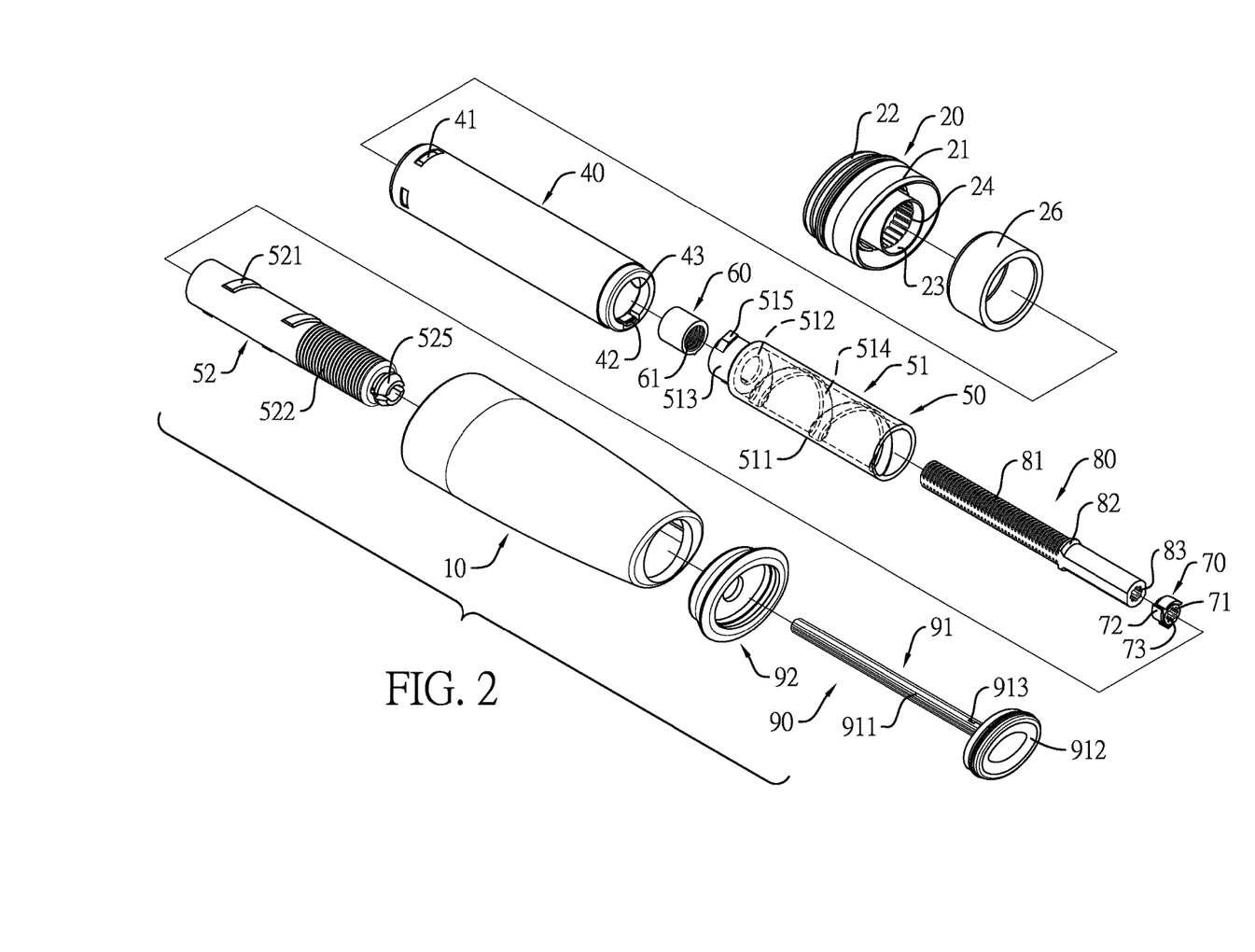
FIG. 2 is another exploded perspective view of the syringe in FIG. 1.

With the reference to FIG. 1 and FIG. 2, a preferred embodiment of a syringe 1 in accordance with the preset invention is shown for combining with a vial 2, a needle 3 and a needle cap 4. The syringe 1 mainly includes an outer protecting housing 10, a connecting ring 20, a vial housing 30, an inner tube 40, a bidirectional guiding tube device 50, a screwing sleeve 60, a ratchet 70, a spiral pushing rod 80, and an injection rod unit 90, or, the syringe 1 further includes a cap 5.

With reference to FIG. 1 and FIG. 2, the outer protecting housing 10 is tubular and has two openings respectively in a front end and a rear end of the outer protecting housing 10. A connecting end 11 is formed at the front end of the outer protecting housing 10.

Figure 3:
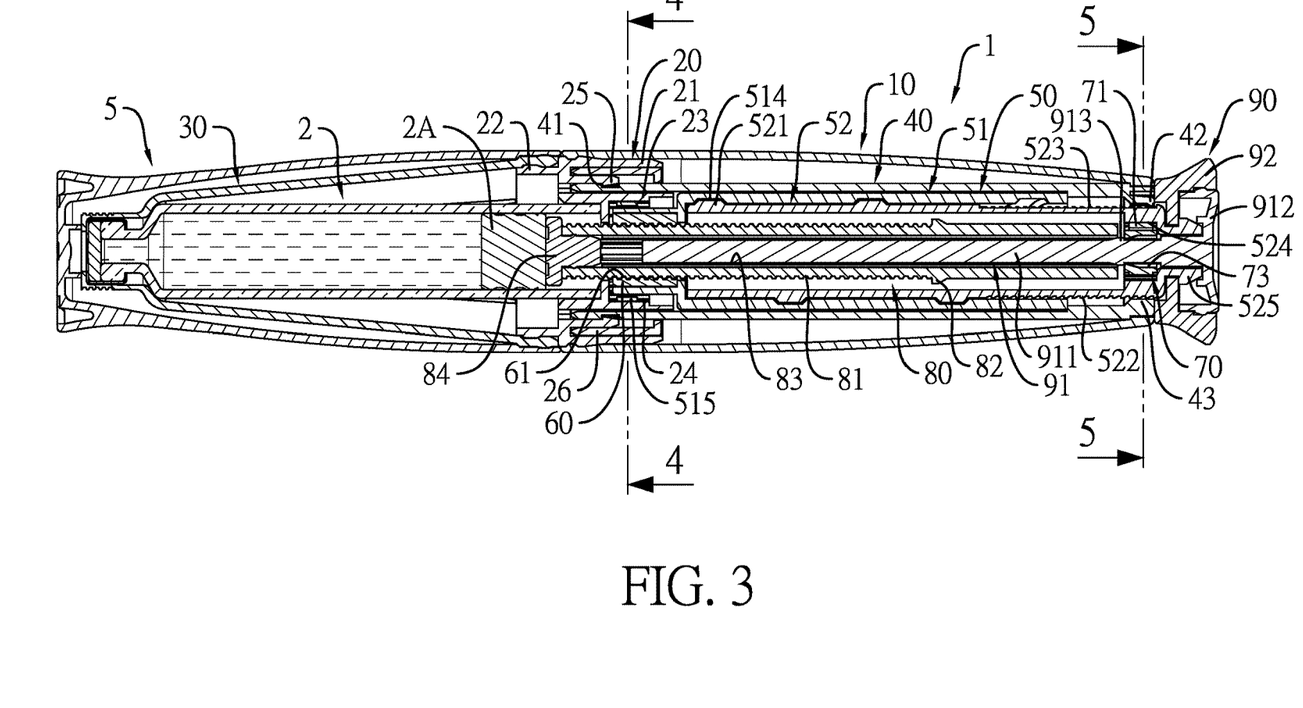
FIG. 3 is a cross-sectional front view of the syringe in FIG. 1, wherein the needle and the needle cap are not mounted on the syringe.

With reference to FIG. 1 and FIG. 2, the connecting ring 20 has a connecting ring portion 21, an assembling ring portion 22, and an inner ring portion 23. The assembling ring portion 22 and the connecting ring portion 21 are respectively formed on a front end and a rear end of the connecting ring 20. The inner ring portion 23 is formed inside the connecting ring 20. The connecting ring portion 21 of the connecting ring 20 is inserted into and is assembled with the connecting end 11 of the outer protecting housing 10. A ratchet portion 24 is formed around an inner surface of the inner ring portion 23 and has multiple inclined teeth. With reference to FIG. 3, in the preferable embodiment, multiple hooks 25 are formed between the inner ring portion 23 and the connecting ring portion 21. The connecting ring 20 further includes an inner ring 26 mounted between the hooks 25 and the inner ring portion 23.

With reference to FIG. 1 and FIG. 2, the vial housing 30 is combined with the connecting ring portion 21 on the front end of the connecting ring 20 for fixing the vial 2 inside. A front end of the vial housing 30 is provided with a needle 3.

With reference to FIG. 1 to FIG. 3, the inner tube 40 is mounted in the outer protecting housing 10. A front end of the inner tube 40 extends into the connecting ring portion 21 of the connecting ring 20 and is mounted around and fixed with the inner ring portion 23. In the preferable embodiment, the front end of the inner tube 40 that extends into the connecting ring 20 has multiple engaging recesses 41. The engaging recesses 41 are engaged with the hooks 25 of the connecting ring 20. The inner ring 26 is mounted around and on the hooks 25 to engage the inner tube 40 with the connecting ring 20. The rear end of the inner tube 40 can extend out of the outer protecting housing 10. A restricting protrusion 42 and a blocking pin 43 are formed on the rear end of the inner tube 40.

With reference to FIG. 1 to FIG. 3, the bidirectional guiding tube device 50 includes an outer guiding tube 51 and an inner guiding tube 52. The outer guiding tube 51 is mounted in the inner tube 40 and has a mounting tube 511. An annular wall 512 is formed on a front end of the mounting tube 511. An end tube 513 axially protrudes from the annular wall 512 toward a front end of the outer guiding tube 51. A spiral recess 514 is formed in and spirally disposed around an inner surface of the mounting tube 511. Multiple ratchet pawls 515 are formed on and arranged around an outer surface of the end tube 513. A positioning channel 516 is axially formed in an inner surface of the end tube 513.

Figure 4:
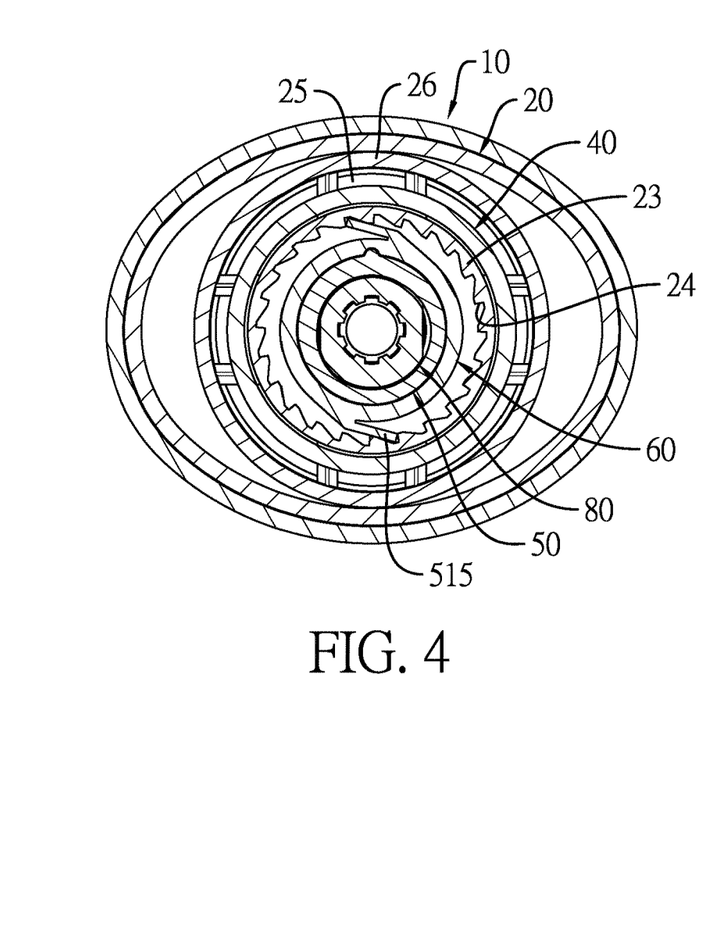
FIG. 4 is a cross-sectional right side view of the syringe along A-A in FIG. 3.

With reference to FIG. 3 and FIG. 4, the end tube 513 extends into the inner ring portion 23 of the connecting ring 20, and the ratchet pawls 515 are engaged with the ratchet portion 24 of the connecting ring 20 to limit the outer guiding tube 51 to rotate only in one single direction.

With reference to FIG. 1 to FIG. 3, the inner guiding tube 52 is mounted in the outer guiding tube 51 and the inner tube 40. The inner guiding tube 52 has multiple spiral protrusions 521 formed on an outer surface of the inner guiding tube 52. The spiral protrusions 521 are mounted in the spiral recess 514. By means of the correspondence between the spiral protrusions 521 and the spiral recess 514, the inner guiding tube 52 can be rotated inside the outer guiding tube 51 for a predetermined movement distance. The inner guiding tube 52 has multiple restricting threaded grooves 522 formed in an outer surface of the inner guiding tube 52 at spaced intervals, and has a guiding recess 523 of a predetermined length. Each of the restricting threaded grooves 522 has a sloped surface. A ratchet recess 524 is formed around the inner surface of the inner guiding tube 52 and has multiple teeth. The teeth orientation of the ratchet recess 524 is same as the teeth orientation of the ratchet portion 24. A pivot portion 525 is formed on a rear end of the inner guiding tube 52 and extends out of the inner tube 40. The position of the restricting protrusion 42 in the rear end of the inner tube 40 can be changed between the restricting threaded grooves 522 in a rear section of the inner guiding tube 52 and the guiding recess 523.

Figure 5:
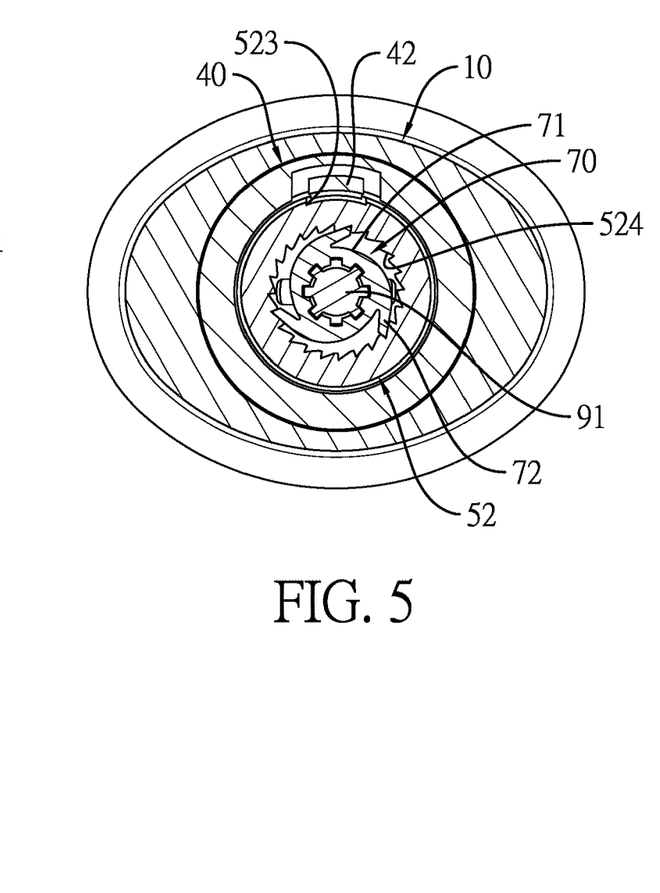
FIG. 5 is a cross-sectional left side view of the syringe along B-B in FIG. 3.

With reference to FIG. 3 and FIG. 5, when the restricting protrusion 42 extends into the guiding recess 523, the inner guiding tube 52 can axially move forward. When the restricting protrusion 42 abuts the restricting threaded grooves 522, the inner guiding tube 52 can be blocked from moving straight forward when the inner guiding tube 52 is accidently pressed.

With reference to FIG. 1 to FIG. 3, the screwing sleeve 60 is axially mounted in the end tube 513 of the outer guiding tube 51. A screw hole 61 is formed in the screwing sleeve 60. The pitch of the screw hole 61 is smaller than the pitch of the spiral recess 514. Preferably, a positioning protrusion 62 is axially formed on an outer surface of the screwing sleeve 60 and corresponds to the positioning channel 516 of the outer guiding tube 51 for engaging the screwing sleeve 60 with the outer guiding tube 51.

With reference to FIG. 1 to FIG. 3, the ratchet 70 is mounted in the ratchet recess 524 of the inner guiding tube 52. The ratchet 70 includes a gear body 71 and multiple ratchet pawls 72 formed around an outer surface of the gear body 71. A central hole 73 is formed in the gear body 71. The shape of the central hole 73 corresponds to the shape of a non-circular axial hole 83 of the spiral rotating rod 80. The ratchet pawls 72 of the ratchet 70 and the ratchet pawls 515 of the outer guiding tube 51 have the same teeth orientation. With reference to FIG. 5, the ratchet pawls 72 are engaged with the teeth of the ratchet recess 524.

With reference to FIG. 1 to FIG. 3, the spiral rotating rod 80 has a dose metering section 81 having screw threads formed around the dose metering section 81. A restricting flange 82 is formed on a side edge of the dose metering section 81 adjacent a center segment of the spiral rotating rod 80. The axial hole 83 is non-circular and is formed in the spiral rotating rod 80. The spiral rotating rod 80 is mounted in the bidirectional guiding tube device 50. The dose metering section 81 of the spiral rotating rod 80 is connected inside the screwing sleeve 60 and extends into the vial 2 to push the piston 2A. Or, a piston pushing block 84 can be mounted on a front end of the dose metering section 81 of the spiral rotating rod 80 to push the piston 2A indirectly.

With reference to FIG. 1 to FIG. 3, the injection rod unit 90 includes an injecting rod 91 and a cover 92. The injecting rod 91 includes a rod body 911 and a pushing end 912 formed at a rear end of the rod body 911. The cross section of the rod body 911 corresponds to the shape of the axial hole 83 of the spiral rotating rod 80 and the shape of the central hole 73 of the ratchet 70. The rod body 911 of the injecting rod 91 is axially movably mounted through the axial hole 83 of the spiral rotating rod 80, and is fixed in the central hole 73 of the ratchet 70. A positioning block 913 is formed on the rod body 911. The ratchet 70 is fixed on the rod body 911 by the positioning block 913. The rear end of the rod body 911 of the injecting rod 91 having the pushing end 912 extends out of the inner guiding tube 52. The cover 92 is mounted around the pushing end 912 of the injecting rod 91. A rear end of the pivot portion 525 of the inner guiding tube 52 is pivotally mounted in the cover 92.

Figure 6:
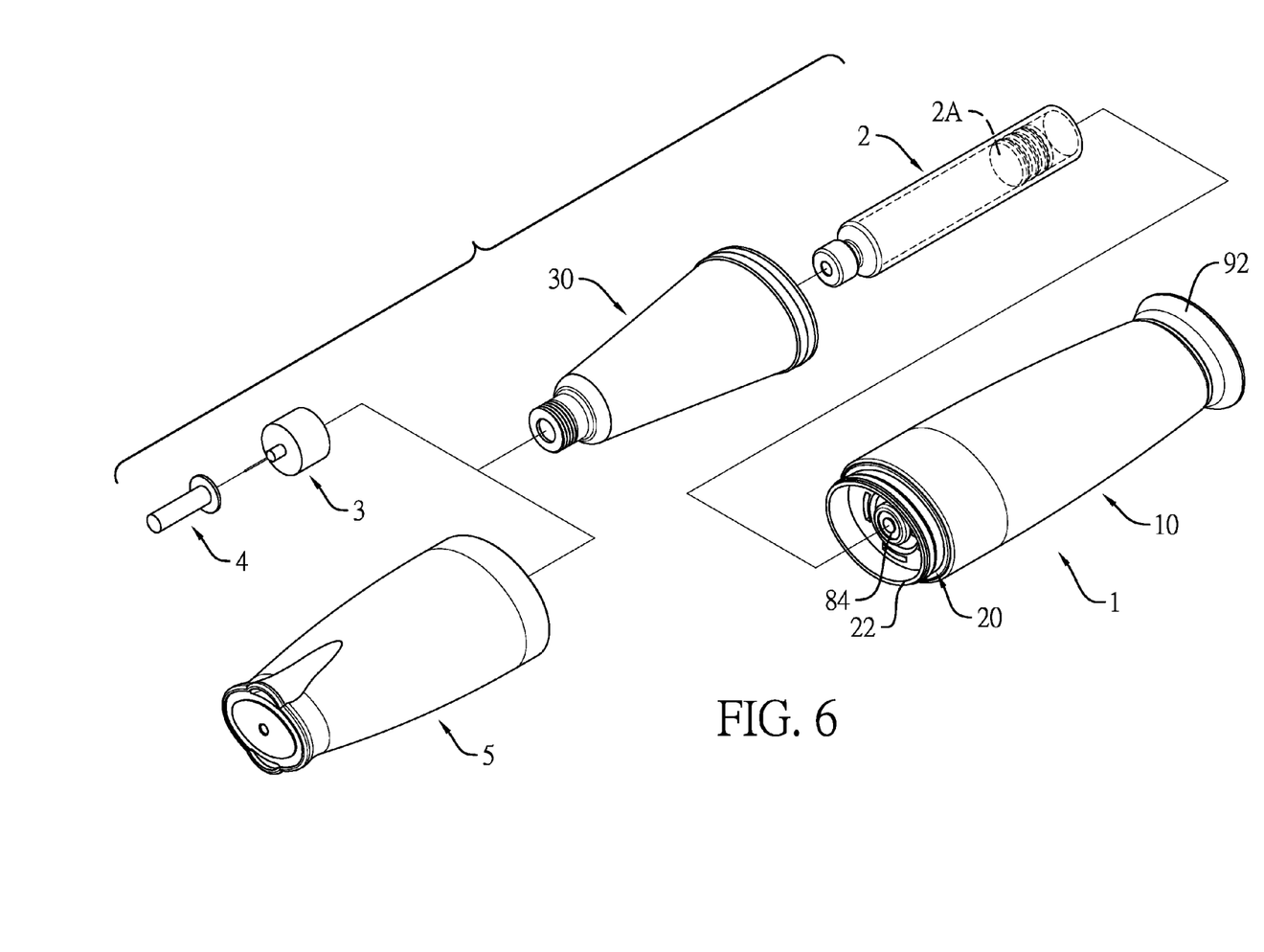
FIG. 6 is a partially exploded perspective view of the syringe in FIG. 1 to FIG. 3, wherein a vial housing is removed and the syringe is shown with a cap, the needle and the needle cap.

Regarding operation of the present invention, with reference to FIG. 3 and FIG. 6, to assemble the vial 2 into the syringe, the vial housing 30 is removed. An end of the vial 2 having the piston 2A extends into and is positioned with the connecting ring 20. The piston pushing block 84 of the spiral rotating rod 80 extends into the vial 2 and abuts the piston 2A. Then the vial housing 30 is mounted around the vial 2. The vial 2 is fixed with the syringe 1 by the vial housing 30 mounted with the connecting ring 20. Before the injection process, the cap 5 is mounted on the vial housing 30. At this time, the needle 3 and the needle cap 4 are disassembled from the vial housing 30 connected with the vial 2.

Figure 7:
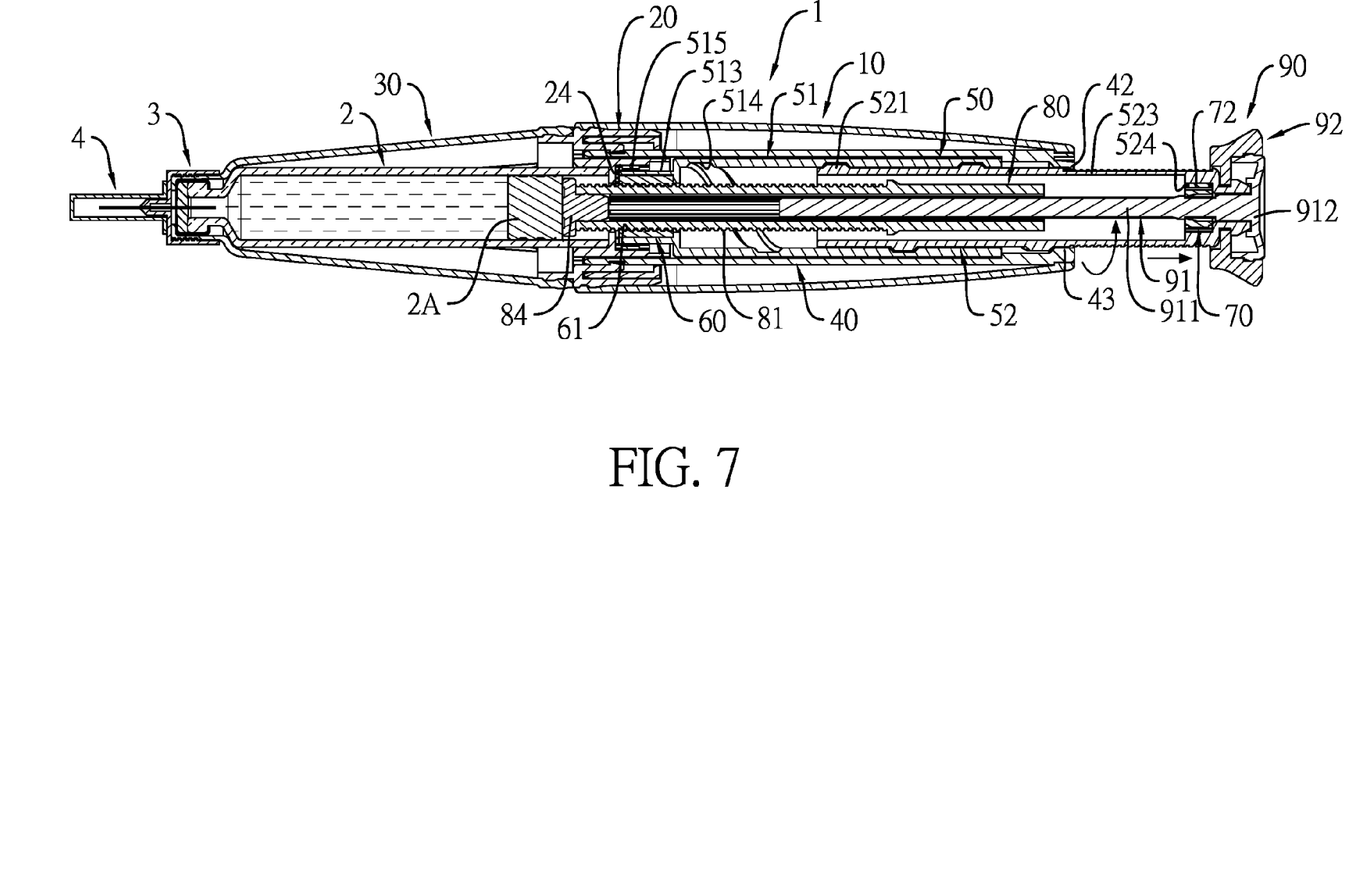
FIG. 7 is a partially exploded perspective view of the syringe in FIG. 1 to FIG. 3, wherein the cap is removed, the syringe is mounted with the needle and the needle cap, and an injection rod is pulled to a predetermined position.

When the injection process is ready, with reference to FIG. 3 and FIG. 7, the cap 5 is removed and the needle 3 and the needle cap 4 are mounted on the syringe. One end of the needle 3 pierces into the vial 2. The needle cap 4 is covered over the needle 3 to prevent a user from being stabbed by the needle 3. Next, the injection rod unit 90 is rapidly pulled backward to a predetermined position till the spiral protrusion 521 of the inner guiding tube 52 moving to and blocked by the blocking pin 43 of the inner tube 40. While the injection rod unit 90 is in a backward pulling process, the inner guiding tube 52 is moved backward and is idly rotated inside the outer guiding tube 51. The restricting protrusion 42 of the inner tube 40 is flicked from the restricting threaded grooves 522 of the inner guiding tube 52 to generate sounds. The inner guiding tube 52 is restricted by the restricting threaded grooves 522 engaged with the restricting protrusion 42 of the inner tube 40 to provide a function that prevents the inner guiding tube 52 from axially moving forward when the injection rod unit 90 is pressed by accident, which can keep the injection rod unit 90 from being retracted accidentally when the injection rod unit 90 is in a pulling process.

Figure 8:
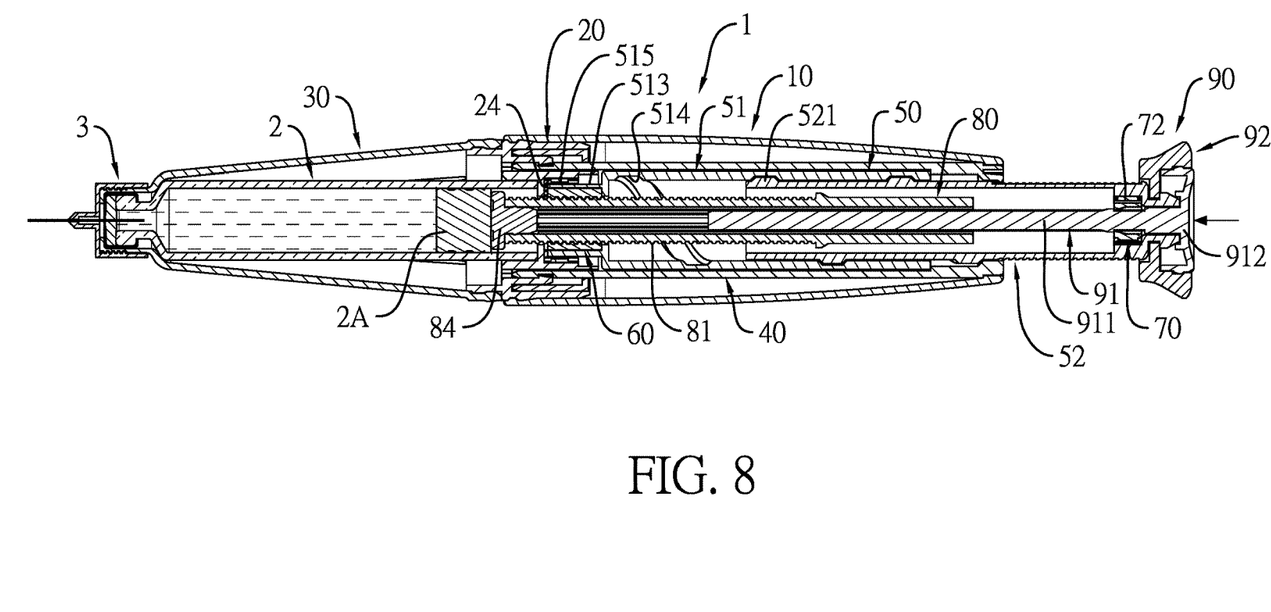
FIG. 8 is a partially exploded perspective view of the syringe in FIG. 1 to FIG. 3, wherein the needle cap is removed and the injection rod is pressed.
Figure 9:
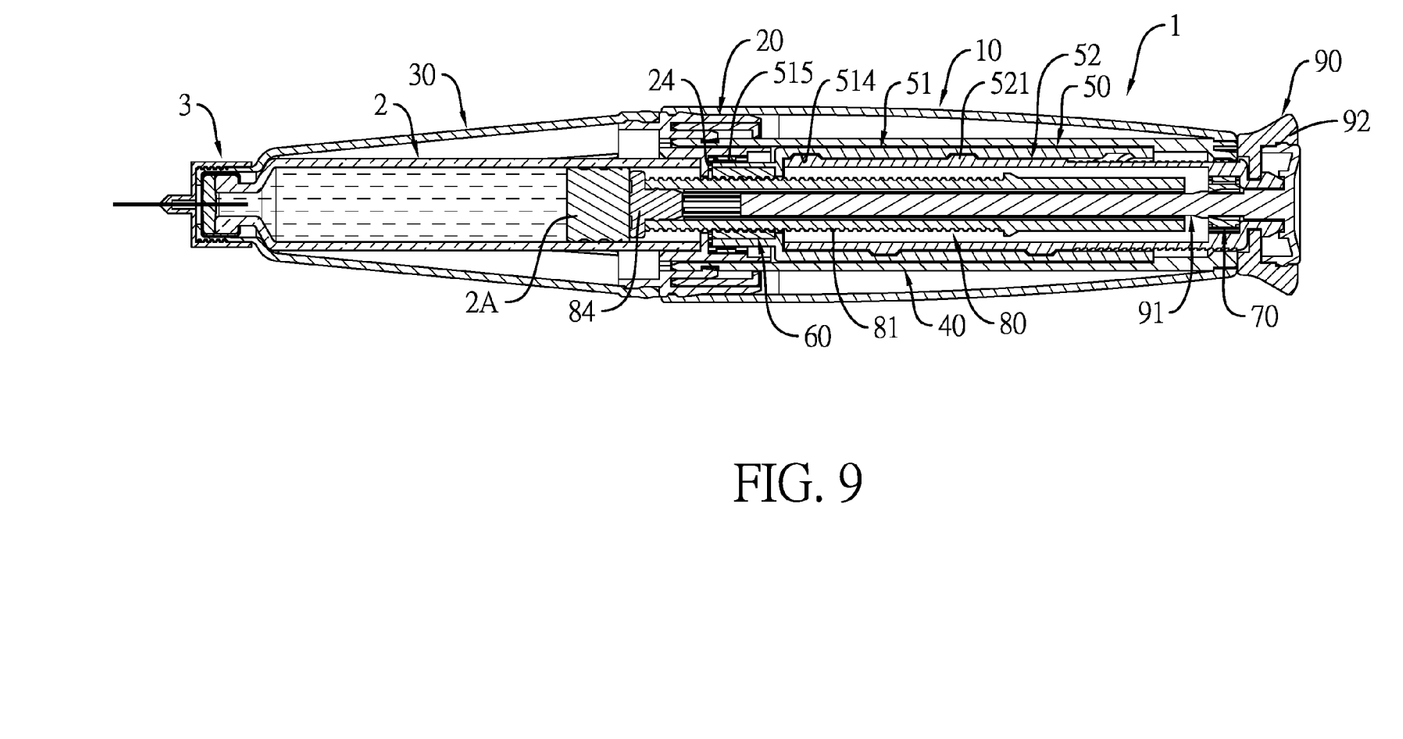
FIG. 9 is a partially exploded perspective view of the syringe in FIG. 1 to FIG. 3, showing a finished state of the injection rod pressed for injection.

In an injecting process, with reference to FIG. 8 and FIG. 9, the needle cap is removed and the needle 3 is pierced into a predetermined position on a human's body, and the injection rod unit 90 is pressed to inject. The inner guiding tube 52 is pushed by the forward movement of pressing the injection rod unit 90 through the cover 92. The restricting protrusion 42 of the inner tube 40 enters the guiding recess 523 of the inner guiding tube 52 to move the inner guiding tube 52 and the injection rod unit 90 forward together. The outer guiding tube 51 is driven to clockwise rotated at a fixed position by the spiral protrusions 521 of the inner guiding tube 52 till the inner guiding tube 52 has moved in the outer guiding tube 51 for a spiral stoke. The injection rod unit 90 extends into and closes the outer protecting housing 10. When the outer guiding tube 51 is clockwise rotated, the screwing sleeve 60 is rotated by the outer guiding tube 51. The spiral rotating rod 80 is driven to rotate and to move forward by the rotating screwing sleeve 60, and pushes the piston 2A of the vial 2. The medication in the vial 2 is discharged by pushing and flows via the needle 3.

As aforementioned, because the spiral recess 514 of the outer guiding tube 51 matches the spiral protrusion 521 of the inner guiding tube 52 and the spiral rotating rod 80 matches the screwing sleeve 60, the injection rod unit 90 can only move straightly for a predetermined distance in one stoke per time by one pressing. When the injection rod unit 90 is pressed, the spiral rotating rod 80 is driven by the screwing sleeve 60 and is rotated with the screwing sleeve 60 to control and to discharge the medication in the vial 2 in a predetermined dose. On the other hand, a large spiral pitch of the combination of the spiral recess 514 of the outer guiding tube 51 and the spiral protrusion 521 of the inner guiding tube 52 matches the small spiral pitch of the combination of a screw hole of the screwing sleeve 60 and the screw threads of the spiral rotating rod 80, because the pushing force of large rotation stroke transfers to the pushing force of small rotation stroke, the syringe 1 is labor-saving in the process of use.

After injection, the needle cap 4 is mounted around the needle 3. The needle cap 4 and the needle 3 are removed together from the syringe 1, and the cap 5 is mounted on the vial housing 30 of the syringe 1 to ensure the needle 3 can be renewed for a next time usage. When the syringe 1 is in use, with the mechanism that the injection rod unit 90 is combined with the ratchet 70, the bidirectional guiding tube device 50, the screwing sleeve 60, and the spiral rotating rod 80, it is convenient for a user's operation by repeating opening and closing in every dose metering injection operating process. The syringe 1 has a dose metering injection function and an automatic frequency-measuring function because injection times and injection doses are set by the volume of the medication in the vial 2 and the numbers of the screw threads and screw pitch of the dose metering section 81 of the spiral rotating rod 80. When the using time of the syringe 1 with the vial 2 approaches the predetermined using time and the medication in the vial 2 is run out in the meantime, the syringe 1 can be replaced to prevent over-use of the syringe 1.

What is claimed is:

1. A syringe used for connecting with a vial and a needle, the syringe comprising:
    an outer protecting housing being tubular and having two openings respectively in a front end and a rear end of the outer protecting housing;
    a connecting ring mounted on the front end of the outer protecting housing and having an inner ring portion, a ratchet portion formed around in the inner ring portion and having multiple inclined teeth;
    a vial housing mounted on a front end of the connecting ring for fixing the vial inside, the needle detachably mounted on a front end of the vial housing;
    an inner tube mounted in the outer protecting housing, a front end of the inner tube fixed in the connecting ring;
    a bidirectional guiding tube device including
        an outer guiding tube having
            a mounting tube and an end tube formed in a front end of the mounting tube;
            a spiral recess formed in an inner surface of the mounting tube;
            multiple ratchet pawls mounted around an outer surface of the end tube and engaged with the ratchet portion of the connecting ring to limit the outer guiding tube to rotate toward one single direction; and
        an inner guiding tube mounted between the outer guiding tube and the inner tube and having
            multiple spiral protrusions formed on an outer surface of a front segment of the inner guiding tube and mounted in the spiral recess to make the inner guiding tube rotate in the outer guiding tube for a predetermined movement distance; and
            a ratchet recess formed in a rear segment of the inner guiding tube and having multiple teeth;
    a screwing sleeve mounted in the end tube of the outer guiding tube and having a screw hole formed in the screwing sleeve;
    a ratchet mounted in the ratchet recess of the inner guiding tube and including a gear body and multiple ratchet pawls formed around an outer surface of the gear body, a central hole formed in the gear body, the ratchet pawls of the ratchet engaged with the teeth of the ratchet recess of the inner guiding tube;
    a spiral rotating rod having a dose metering section having screw threads formed around the dose metering section, an axial hole formed in the spiral rotating rod, the spiral rotating rod mounted in the bidirectional guiding tube device, the dose metering section connected inside the screwing sleeve and extending into the vial to generate a push force; and
    an injection rod unit including
        an injecting rod including a rod body and a pushing end formed at a rear end of the rod body, the rod body axially movably mounted through the axial hole of the spiral rotating rod and fixed in the central hole of the ratchet, the rear end of the rod body that has the pushing end extending out of the inner guiding tube; and
        a cover mounted around the pushing end of the injecting rod, a rear end of the inner guiding tube pivotally mounted in the cover to combine the ratchet, the bidirectional guiding tube, the screwing sleeve and the spiral rotating rod for opening and closing repeatedly.

2. The syringe as claimed in claim 1, wherein
    the inner tube has a restricting protrusion and a blocking pin formed in a rear end of the inner tube;
    the inner guiding tube has multiple restricting threaded grooves formed in an outer surface of the inner guiding tube at spaced intervals, and has a guiding recess of a predetermined length;
    the restricting protrusion abuts the restricting threaded grooves of the inner guiding tube to block the inner guiding tube from moving forward;
    the restricting protrusion changes positions to abut the guiding recess to drive the inner guiding tube to move forward; and
    the restricting protrusion limits the position of backward moving of the inner guiding tube.

3. The syringe as claimed in claim 2, wherein a shape of the axial hole of the spiral rotating rod corresponds to a shape of the rod body of the injecting rod, and both of the shapes are non-circular.

4. The syringe as claimed in claim 2, wherein the screwing sleeve has a positioning protrusion axially formed on an outer surface of the screwing sleeve;
    the outer guiding tube has a positioning channel axially formed in an inner surface of the end tube;
    the screwing sleeve is engaged with the outer guiding tube by the positioning protrusion corresponding to mount in the positioning channel.

5. The syringe as claimed in claim 4, wherein an assembling ring portion and a connecting ring portion are respectively formed in the front end and a rear end of the connecting ring;
    the connecting ring portion is inserted into the outer protecting housing;
    multiple hooks are formed between the inner ring portion and the connecting ring portion;
    the inner tube has multiple engaging recesses for the hooks to engage;

an inner ring is mounted between the hooks and the inner ring portion to connect the inner tube and the connecting ring.

6. The syringe as claimed in claim 5, wherein a piston pushing block is mounted in a front end of the dose metering section of the spiral rotating rod.

7. The syringe as claimed in claim 1, wherein a shape of the axial hole of the spiral rotating rod corresponds to a shape of the rod body of the injecting rod, and both of the shapes are non-circular.

8. The syringe as claimed in claim 1, wherein the screwing sleeve has a positioning protrusion axially formed on an outer surface of the screwing sleeve;
the outer guiding tube has a positioning channel axially formed in an inner surface of the end tube;
the screwing sleeve is engaged with the outer guiding tube by the positioning protrusion corresponding to mount in the positioning channel.

9. The syringe as claimed in claim 8, wherein an assembling ring portion and a connecting ring portion are respectively formed in the front end and a rear end of the connecting ring;
the connecting ring portion is inserted into the outer protecting housing;
multiple hooks are formed between the inner ring portion and the connecting ring portion;
the inner tube has multiple engaging recesses for the hooks to engage;
an inner ring is mounted between the hooks and the inner ring portion to connect the inner tube and the connecting ring.

10. The syringe as claimed in claim 9, wherein a piston pushing block is mounted in a front end of the dose metering section of the spiral rotating rod.

\* \* \* \* \*

UNITED STATES PATENT AND TRADEMARK OFFICE
CERTIFICATE OF CORRECTION

PATENT NO. : 10,149,944 B2
APPLICATION NO. : 15/274814
DATED : December 11, 2018
INVENTOR(S) : Chin-Min Yeh Page 1 of 1

It is certified that error appears in the above-identified patent and that said Letters Patent is hereby corrected as shown below:

On the Title Page

Item (22), should read:
(22) PCT Filed: Apr. 3, 2014

Item (86), should read:
(86) PCT No.: PCT/CN2014/074713
§ 371 (c)(1),
(2) Dated: Sept. 23, 2016

Item (87), should read:
(87) PCT Pub. No.: WO2015/149323
PCT Pub. Date: Oct. 8, 2015

Signed and Sealed this
Twenty-ninth Day of October, 2019

Andrei Iancu
*Director of the United States Patent and Trademark Office*

UNITED STATES PATENT AND TRADEMARK OFFICE
CERTIFICATE OF CORRECTION

PATENT NO.       : 10,149,944 B2
APPLICATION NO.  : 15/274814
DATED            : December 11, 2018
INVENTOR(S)      : Chin-Min Yeh Page 1 of 1

It is certified that error appears in the above-identified patent and that said Letters Patent is hereby corrected as shown below:

On the Title Page

Item (63) should read:
(63) Continuation of application No. PCT/CN2014/074713, filed on Apr. 3, 2014.

Signed and Sealed this
Twenty-sixth Day of November, 2019

Andrei Iancu
*Director of the United States Patent and Trademark Office*

UNITED STATES PATENT AND TRADEMARK OFFICE
CERTIFICATE OF CORRECTION

| | |
|---|---|
| PATENT NO. | : 10,149,944 B2 |
| APPLICATION NO. | : 15/274814 |
| DATED | : December 11, 2018 |
| INVENTOR(S) | : Chin-Min Yeh |

It is certified that error appears in the above-identified patent and that said Letters Patent is hereby corrected as shown below:

This certificate supersedes the Certificate of Correction issued October 29, 2019. The certificate was issued prematurely and is vacated since the Petition under CFR 1.78 dated September 19, 2019 was dismissed by deciding official in the Office of Petitions. The Certificate of Correction dated October 29, 2019, was published in error and should not have been issued for this patent.

Signed and Sealed this
Eighteenth Day of February, 2020

Andrei Iancu
*Director of the United States Patent and Trademark Office*

UNITED STATES PATENT AND TRADEMARK OFFICE
CERTIFICATE OF CORRECTION

| | | |
|---|---|---|
| PATENT NO. | : 10,149,944 B2 | Page 1 of 1 |
| APPLICATION NO. | : 15/274814 | |
| DATED | : December 11, 2018 | |
| INVENTOR(S) | : Chin-Min Yeh | |

It is certified that error appears in the above-identified patent and that said Letters Patent is hereby corrected as shown below:

This certificate supersedes the Certificate of Correction issued November 26, 2019. The certificate was issued prematurely and is vacated since the Petition under CFR 1.78 dated September 19, 2019 was dismissed by deciding official in the Office of Petitions. The Certificate of Correction dated November 26, 2019, was published in error and should not have been issued for this patent.

Signed and Sealed this
Seventeenth Day of March, 2020

Andrei Iancu
*Director of the United States Patent and Trademark Office*